United States Patent
Ikeda et al.

(10) Patent No.: US 7,002,684 B2
(45) Date of Patent: Feb. 21, 2006

(54) PARTICLE SIZE DISTRIBUTION MEASURING METHOD, DEVICE, AND PROGRAM FOR COMPENSATING FOR PARTICLE CONCENTRATION

(75) Inventors: Hideyuki Ikeda, Kyoto (JP); Yoshiaki Togawa, Kyoto (JP)

(73) Assignee: Horiba, Ltd., Kyoto (JP)

( * ) Notice: Subject to any disclaimer, the term of this patent is extended or adjusted under 35 U.S.C. 154(b) by 383 days.

(21) Appl. No.: 10/623,247

(22) Filed: Jul. 18, 2003

(65) Prior Publication Data

US 2004/0075833 A1  Apr. 22, 2004

(30) Foreign Application Priority Data

Jul. 22, 2002  (JP)  .............................. 2002-211915

(51) Int. Cl.
 *G01N 15/02*  (2006.01)

(52) U.S. Cl. ..................................... 356/336; 356/338
(58) Field of Classification Search .................... None
 See application file for complete search history.

(56) References Cited

U.S. PATENT DOCUMENTS

| | | | |
|---|---|---|---|
| 4,318,180 A * | 3/1982 | Lundqvist et al. ............ | 702/29 |
| 6,010,593 A * | 1/2000 | Eymin Petot Tourtollet et al. ............................ | 162/4 |
| 6,091,492 A * | 7/2000 | Strickland et al. .......... | 356/336 |
| 6,184,517 B1 * | 2/2001 | Sawada et al. .......... | 250/222.2 |
| 6,211,956 B1 * | 4/2001 | Nicoli ........................ | 356/337 |

* cited by examiner

*Primary Examiner*—Michael P. Stafira

(57) ABSTRACT

The present invention provides a particle diameter distribution measuring method, a particle diameter distribution measuring device, and a measuring program which decreases the dependence of the calculation of particle diameter distribution on sample concentration, and can measure with higher precision by setting a concentration correction unique to a specific measuring sample in a particle diameter distribution measuring device. The measuring sample is measured by changing its concentration. Concentration correction constants for correcting detection values of detectors according to the concentration of the sample are found. The detection values of the respective detectors are corrected by using the concentration correction constants, and the particle diameter distribution is measured by using the corrected detection values of the respective detectors.

12 Claims, 11 Drawing Sheets

PARTICLE SIZE DISTRIBUTION MEASURING METHOD, DEVICE, AND PROGRAM FOR COMPENSATING FOR PARTICLE CONCENTRATION

FIELD OF THE INVENTION

The present invention relates to a particle size distribution measuring method, a particle size distribution measuring device, and a measuring program for a particle size distribution measuring device that addresses variation in particle concentrations in a sample.

DESCRIPTION OF THE RELATED ART

Particle size distribution is measured by a conventional particle diameter distribution measuring device as follows: a measuring sample is irradiated with light and the diffraction light and/or scattered light are/is detected by plural detectors (having individual channels) arranged around the measuring sample. The intensity distribution in the diffraction light and/or scattered light is found at each angle from the detection values corresponding to the channels of the detectors and the particle diameter distribution is analyzed and calculated by using the intensity distribution in the scattered light.

In general, the operator of a particle diameter distribution measuring device analyzes and calculates the particle diameter distribution which matches the measuring sample after inputting the value of the refractive index according to the measuring sample and then adjusting the concentration of the measuring sample to the proper range for the measurement of the particle diameter distribution by, for example, diluting the measuring sample. On the other hand, all the constants used for the analysis of the particle diameter distribution such as the sensitivity of the detectors, excluding the refractive index, are fixed to the values set at the time of shipment of the device. However, it is known that the intensity distribution in the scattered light to be measured is affected by not only the refractive index of the measuring sample but also various other properties, and is particularly varied largely depending on the particular concentration of particles in the measuring sample. Therefore, it has been important for the accurate analysis of particle diameter distribution to adjust the concentration of the measuring sample to a proper range for an analysis of particle diameter distribution by diluting the measuring sample or other adjustment approaches.

Generally conventional measuring devices do not incorporate a feature of correcting the intensity of scattered light by adjusting for concentration levels of particles in a sample and those that address this issue usually assume a universal adjustment common to all possible samples.

SUMMARY OF THE INVENTION

The present invention has an object of providing a particle size distribution such as a particle diameter distribution measuring method, a particle diameter distribution measuring device, and a measuring program for a particle diameter distribution measuring device which can decrease dependence of calculating the particle diameter distribution on the sample concentration, and can measure at a higher precision by setting a concentration correction unique to a specific measuring sample in a particle diameter distribution measuring device.

In order to achieve the above object, the particle diameter distribution measuring method of an embodiment is characterized in that in a particle diameter distribution measuring device for measuring the particle diameter distribution of a measuring sample, based on the detection values of plural detectors provided for detecting at predetermined angles, diffracted light and/or scattered light generated when light is applied to the measuring sample, on the basis of detection values of the respective detectors in which the measuring sample is measured by changing its concentrations, concentration correction constants for correcting the detection values of the respective detectors according to the concentrations of the sample are found, the detection values of the respective detectors are corrected by using the concentration correction constants, and particle diameter distribution is measured by using the corrected detection values of the respective detectors.

Since the concentration correction constants are found in accordance with the variously changed concentrations of the measuring sample based on measuring the sample in various concentrations, correcting the detection values of the detectors by using the concentration correction constants can remove with high precision an influence of error resulting from a specific concentration of the measuring sample. In other words, the concentration correction constants are found and used separately for each measuring sample and for each detector, so the particle diameter distribution can be analyzed accurately even when the measuring sample has a high concentration.

Since the concentration correction constants are found from the measuring sample for the same kind of sample, it becomes possible to substantially remove all the influence of distortion, which changes depending on the concentration of the sample and is different depending not only on the refractive index of the measuring sample but also on its shape, size, optical properties, and particle diameter distribution. This enables a particle diameter distribution measurement with a higher precision.

The particle diameter distribution measuring device of a second embodiment includes a storage member which stores the detection values of the detectors separately for each concentration level when the measuring sample, diluted to different concentrations, is measured, and an arithmetic processing part provided with the function of generating concentration correction constants which retrieves stored concentration correction constants for removing the influence of error resulting from the concentration of the measuring sample separately for each detector by analyzing the detection values of the detectors stored in the storage part in association with the concentrations of the measuring sample.

The use of the particle diameter distribution measuring device can allow a gradual dilution of the concentration of the measuring sample so as to find and store the detection values of the detectors separately for each concentration. The use of the particle diameter distribution measuring device can also find the influence of distortion of the detection values resulting from the concentration of the measuring sample by using the detection values for each concentration. The concentration correction constants can be found separately for each detector to remove the influence of error resulting from the concentration and can be used to obtain analysis results which are not affected by the distortion of the detection values resulting from the concentration when the particle diameter distribution for the same type of sample is to be found as the measuring sample.

The particle diameter distribution measuring device of a third embodiment is a device for measuring the particle diameter distribution of a measuring sample, based on the detection values of plural detectors provided for detecting at every predetermined angle diffraction light and/or scattered light generated when light is applied to the measuring sample, the device comprising: a storage member which stores concentration correction constants obtained by finding the amount of correction in the detection values of the detectors in accordance with the concentrations of the measuring sample, based on detection values of the detectors measured a plural number of times by changing the concentration of the measuring sample, and an arithmetic processing part which corrects the detection values of the detectors in accordance with the concentrations of the measuring sample by using the concentration correction constants, and then calculates the particle diameter distribution by using the corrected detection values.

Thus, the detection values of the detectors can be properly corrected by concentration correction constants stored in the storage member separately for each detector, and the distortion of the detection values resulting from the concentration, such as multiple scattering or absorption can be removed effectively. This improves the precision of the analysis results of the particle diameter distribution. Furthermore, since there is no need for dilution in order to adjust the concentration of the measuring sample to a proper range for particle diameter distribution, the measuring procedure is simplified.

Therefore, combining the particle diameter distribution measuring device of the second embodiment and the particle diameter distribution measuring device of the third embodiment makes it possible to store the detection values of the detectors separately for each concentration value, and to correct the detection values stored separately for each concentration and for each detector so as to analyze the particle diameter distribution. This realizes a determination of the particle diameter distribution with high precision which is free from the influence of error resulting from the concentration of the measuring sample.

The measuring program of the particle diameter distribution measuring device of the fourth embodiment is a program to be executed by the particle diameter distribution measuring device for measuring the particle diameter distribution of a measuring sample, based on the detection values of plural detectors provided for detecting at every predetermined angle diffraction light and/or scattered light generated when light is applied to the measuring sample, the program being composed of a detection value grabbing program for measuring a measuring sample diluted to different concentrations and storing the detection values of the detectors separately for each concentration; and a correction constant generation program for analyzing the detection values of the detectors in association with the concentrations of the measuring samples, and for finding the concentration correction constants for each detector which remove the influence of error resulting from concentration.

Thus, through the execution of the measuring program of the particle diameter distribution measuring device, the measuring sample is diluted to different concentrations and measured to find the concentration correction constants that correspond to the detectors, and when the particle diameter distribution of the same sample as the measuring sample is going to be found, an arithmetic processing can be performed without being affected by the distortion of the detection values resulting from the concentration.

The correction constant generation program comprises an approximate curve calculation step for finding an approximate curve indicative of the relation between the detection values and the concentration of a measuring sample; an ideal value calculation step for finding the ideal proportionality indicative of the relation between the detection values and the concentration of the measuring sample from the inclination of the approximate curve at the time when the concentration is substantially zero; and a correction constant generation step for finding the concentration correction constant to remove the influence of error resulting from the concentration based on the difference of the detection values with respect to the ideal proportionality. The relation between the ideal concentration and the detection values is found by making use of the feature that as the concentration of the sample approaches zero, the influence of multiple scattering or attenuation reduces remarkably and also by making use of the proportionality between the ideal concentration and the detection values. Then, the size of error resulting from the concentration is determined from the amount of distortion with respect to the proportionality so as to find the concentration correction constant accurately.

The measuring program of the particle diameter distribution measuring device of a fifth embodiment is a program to be executed by the particle diameter distribution measuring device for measuring the particle diameter distribution of a measuring sample, based on the detection values of plural detectors provided for detecting at every predetermined angle diffraction light and/or scattered light generated when light is applied to the measuring sample, on the basis of detection values of the respective detectors in which the measuring sample is measured by changing its concentrations, concentration correction constants found according to each concentrations of the sample is used, thereby performing a correction to remove the influence of error resulting from the concentration from the detection values of the detectors according to the concentrations of the measuring sample, and particle diameter distribution is measured by using the corrected detection values.

Thus, the execution of the measuring program expands the acceptable range of the concentration of the measuring sample that is measurable by the particle diameter distribution measuring device, thereby facilitating the measurement and improving the precision of the measured results. Since the measuring program can be executed by conventional particle diameter distribution measuring devices, appropriate recording media such as CD-ROM or floppy disk can be introduced to the conventional particle diameter distribution measuring devices so as to improve its workability and precision.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the intention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

The inventors of the present invention have filed for (not open to the public at the time of filing the application of the present invention) a particle diameter distribution measuring device (Japanese Patent Application No. 2001-043303) which achieves improved measuring precision, regardless of the concentration of the measuring sample by removing the influence of error resulting from the concentration of the measuring sample, such as the attenuation of scattered light or multiple scattering. This particle diameter distribution measuring device removes the influence of the attenuation of scattered light and multiple scattering by correcting the detection values on the intensities of the scattered light in correspondence to the respective scattering angles by using the amount of attenuation of transmitted light which is obtained from the measurement values of the light intensities detected by the detectors on the light axes of the light source.

However, even if the amount of attenuation of the transmitted light is the same, it is inevitable that different measuring samples have different patterns of distribution in the scattered light intensity which change with the concentration of the measuring sample, because measuring samples can be different in shape, size, optical properties including the refractive index, and the particle diameter distribution. For example, in the case of particles with small diameters, multiple scattering sometimes becomes influential even with a small amount of attenuation of transmitted light. In addition, there is a tendency that multiple scattering hardly occurs in the case of a low concentration, but becomes very influential in the case of a high concentration.

Figure 1:
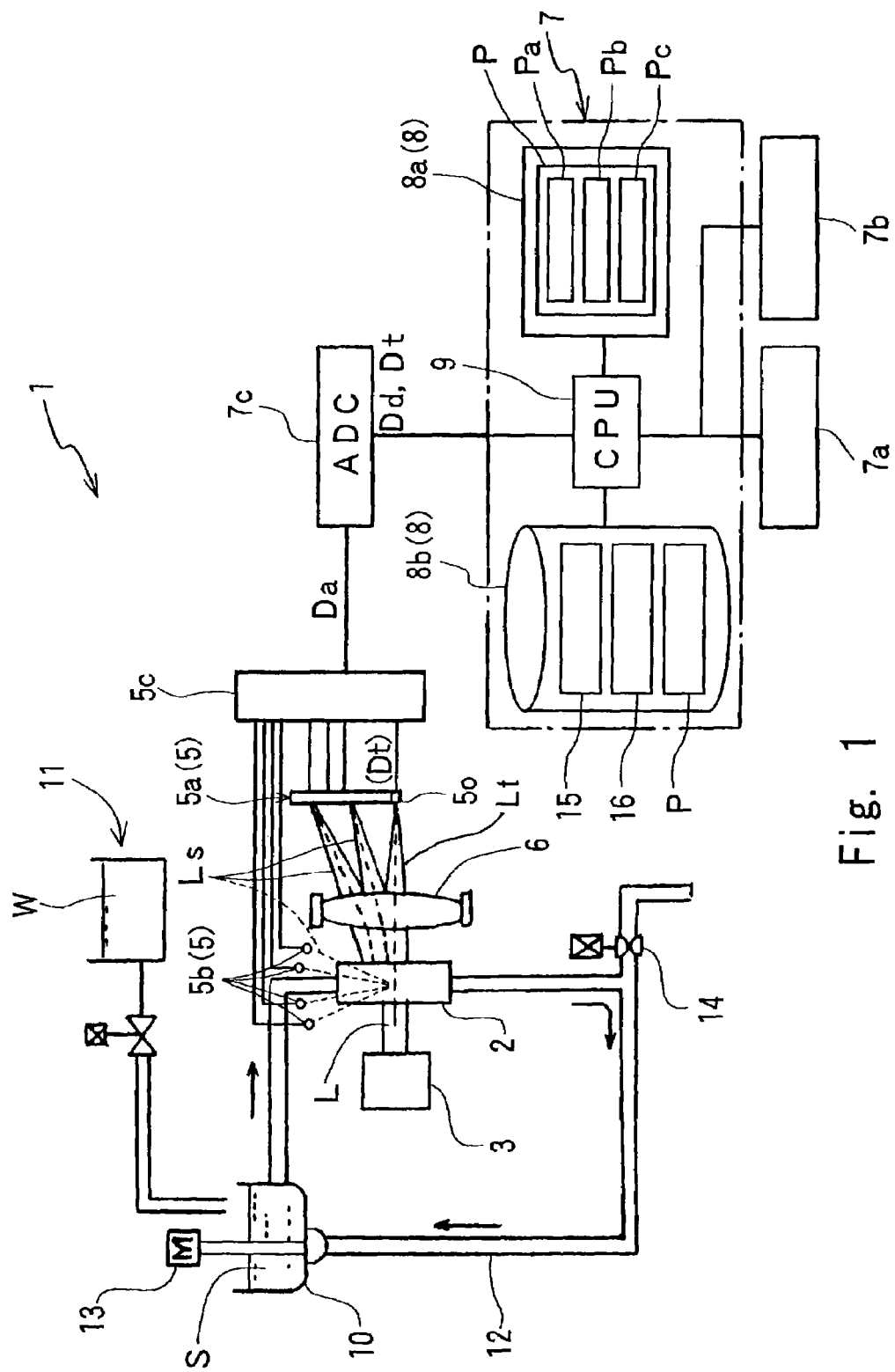
FIG. 1 shows a schematic of a particle diameter distribution measuring device of the present invention.

FIG. 1 shows a diagrammatic illustration of the components of the particle diameter distribution measuring device 1 of the present invention. In FIG. 1, the reference numeral 2 represents a measuring cell which accommodates a measuring sample S in a scattered state; the reference numeral 3 represents a radiation unit such as a He-Ne laser tube which applies laser light L to the cell 2; the reference numerals 5 represent detectors (the detector 5 positioned ahead in the direction of travel of the laser light L is referred to as the detector 5a, and the detectors 5 at a side or behind in the direction of travel of the laser light L are referred to as the detectors 5b) which detect diffraction light and/or scattered light (hereinafter, diffraction light and scattered light are collectively referred to as scattered light Ls) generated by the measuring sample S; and the reference numeral 6 represents a lens for collecting the laser light L on the detector 5a.

The present embodiment shows the case where the detector 5a is a ring detector and is provided with a detector 5o for detecting the transmitted light Lt arranged in the center; however, this is not essential for the present invention. Furthermore, each layer of the ring detector 5a and each of the detectors 5b are assigned with different channels, and the detectors 5 as a whole output the detection values of the amount of light in the respective channels. Therefore, in the following description, the detection value in each channel is expressed as the detection value of each detector 5. The detection signal Da of each channel in the detectors 5 is selectively outputted by a multiplexer 5c or the like.

The reference numeral 7 represents an arithmetic processing unit which calculates the particle diameter distribution of the measuring sample S by using the detection signal Da (which is an analog value and is digital-converted into a detection value Dd) of the scattered light Ls detected by each detector 5. The arithmetic processing unit 7 is provided with a storage part or member 8 and a processing part 9 (hereinafter referred to as CPU) which finds the particle diameter distribution of the measuring sample S by analyzing the intensity of the scattered light Ls detected by each detector 5 while using a program and data stored in the storage part 8.

The reference numeral 7a represents a display device which displays the obtained particle diameter distribution and the like; the reference numeral 7b represents an input device such as keyboard or a pointing device (e.g., a mouse) which inputs instructions from the operator; the reference numeral 7c represents an AD converter which converts an analog detection signal Da from each detector 5 into a digital detection value Dd and forwards it to the arithmetic processing unit 7. The AD converter 7c and the multiplexer 5c could be integrated as one unit.

The reference numeral 10 represents an accommodator which accommodates the measuring sample S; the reference numeral 11 represents a concentration level adjusting unit or a diluting unit which dilutes the measuring sample S accommodated in the accommodator 10 to an appropriate concentration of particles to carrier medium; the reference numeral 12 represents a communicating tube which flows the measuring sample S in the accommodator 10 to the test cell 2; the reference numeral 13 represents a pump which circulates and stirs the measuring sample S in the communicating tube 12; and the reference numeral 14 represents a drain valve which drains the sample S in the communicating tube 12.

The constitution of the device of the present embodiment is just one possible example to make the following description easy to understand, and the present invention is not restricted to this configuration. For example, the shape of the cell 2 is not restricted to be a box, and it can be a cylinder. In addition, the arrangements and numbers of the light source 3 and detectors 5, and the positions and types of the lens 6 can be selected appropriately. Additional components such as an ultrasound distributor can be provided.

The storage part 8 of the present embodiment is composed of a memory 8a for the CPU 9 and a supplemental storage device 8b such as a hard disk. These components of the storage part 8 store detection value files 15 which contain the detection values Dd of the scattered light Ls detected from the detectors 5; concentration correction constant files 16 which store the concentration correction constants obtained from the detection value files 15 in association with the measuring samples S, and measuring programs P which can be executed by the arithmetic processing unit 7.

The measuring program P can be composed of a detection value sample and hold or grabbing program Pa which dilutes a measuring sample S to appropriate predetermined concentrations and grabs the measurement values Dd from the detectors 5 corresponding to the respective concentrations; a correction constant generation program Pb which finds the concentration correction constants by using the grabbed detection value Dd; and a particle diameter distribution analyzing program Pc which finds the particle diameter distribution after correcting the detection values Dd by using the concentration correction constants.

Figure 2:
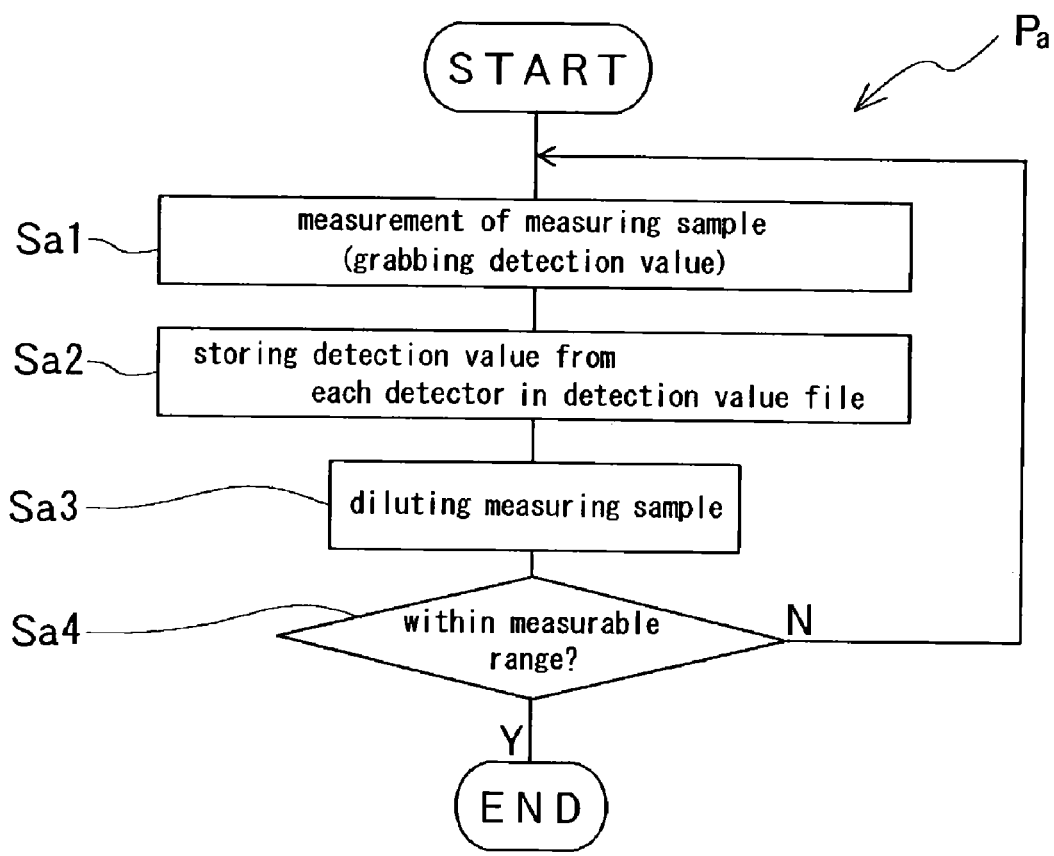
FIG. 2 shows an example of a detection value grabbing program which is executed by the particle diameter distribution measuring device.
Figure 3:
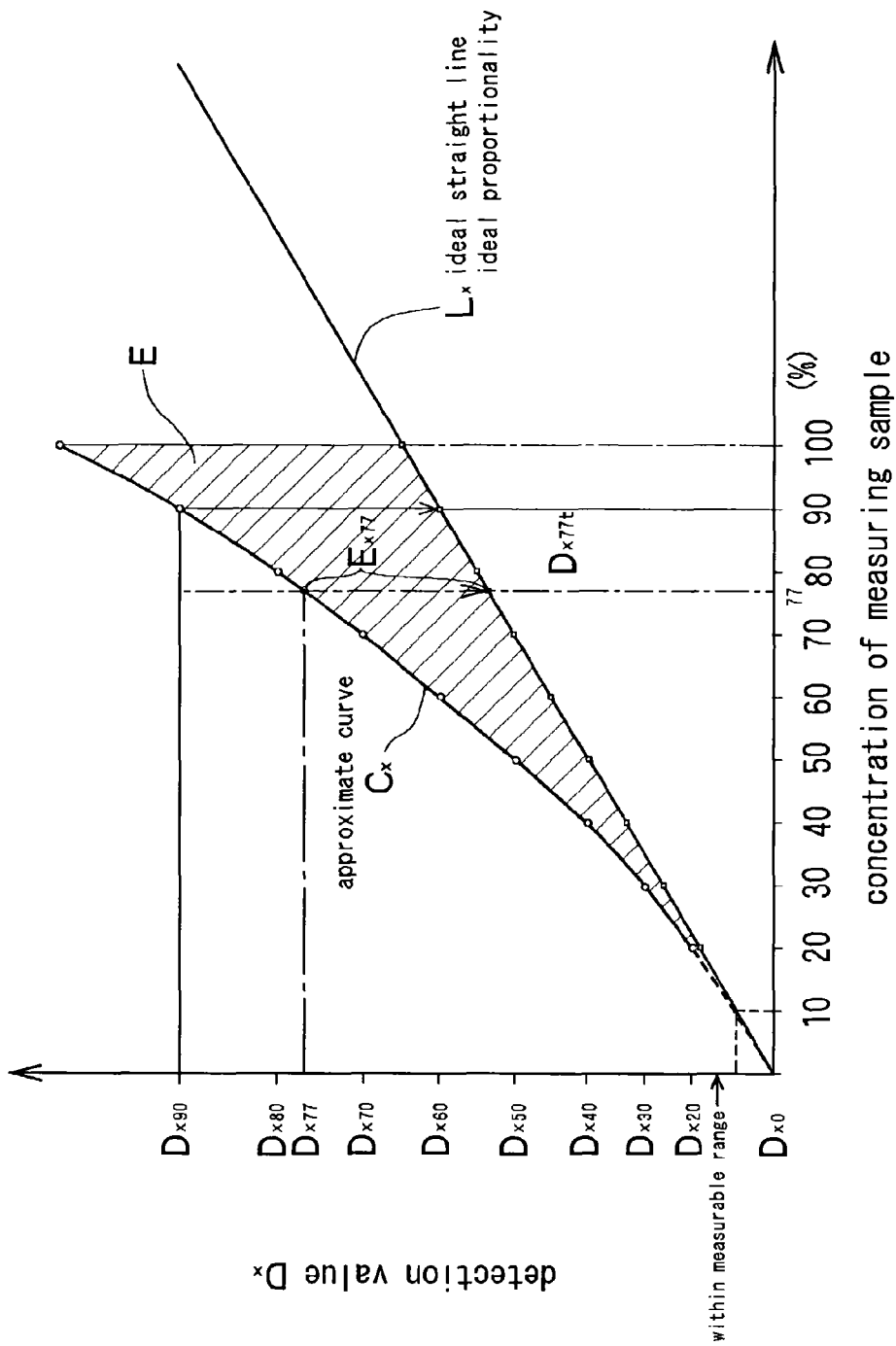
FIG. 3 shows an illustrative relation between the concentration of a measuring sample and the detection value.

FIG. 2 shows the operation of the detection value grabbing program Pa, and FIG. 3 shows, taking the detection value Dd of a specific channel X as an example (for the sake of convenience, the detection value Dd of the channel X is hereinafter referred to as the detection value Dx), of the relation between the concentration and the detection value Dx from the detectors 5.

In FIG. 2, Sa1 is a step for grabbing the detection value Dx from each detector 5. To be more specific, when the step Sa1 is first executed, the measuring sample S accommodated in the accommodator 10 is diluted to a predetermined concentration. When the concentration is e.g. 90%) the laser light L is applied to the measuring sample S and the detection value Dd in each channel at this moment is grabbed.

By storing the detection value of the detector 5o which detects the transmitted light rate Lt (the detection value of the transmitted light Lt is hereinafter referred to as Dt) arranged in the center of the ring detector 5a at the time of the concentration 90%, it can be used as an index for monitoring the concentration of the measuring sample S. Assume that as shown in FIG. 3, the detection value Dx of the detector 5 in the channel X is Dx90 when the laser light L is applied to the measuring sample S having a concentration of 90%.

Sa2 shown in FIG. 2 indicates a step for storing the detection value Dd from each detector 5 in the detection value file 15. The concentration of the measuring sample S (initially 90%) measured or the detection value Dt of the transmitted light Lt and the like are stored at the same time in the detection value file 15.

For example, it is possible to assign the detection value file 15 the file name "Smp11_90" so as to identify the type and concentration of the sample from the file name. It goes without saying that the naming of files and expressing the concentrations can be changed variously. Although the present embodiment shows the case where different detection value files 15 are generated for different concentrations, it is possible that one detection value file 15 stores the detection values measured with different concentrations in association with the concentration values.

In any case, even if there is more data than can be stored in the memory 8a, the data can be processed by storing as a detection value file 15 the measurement values measured by changing the concentration of the measuring sample S, and the other programs Pb and Pc can use the detection value file 15 easily. However, the present invention is not restricted to storing the detection value Dd from each detector 5 in the detection value file 15.

Sa3 is a step for diluting the measuring sample S to a predetermined concentration. During this step, the arithmetic processing unit 7 dilutes the concentration at the rate of e.g. 10%, by properly draining the measuring sample S through the drain valve 14 or by introducing a dispersion medium W (See FIG. 1) while controlling the automatic diluting unit 11. Thus, the use of the automatic diluting unit 11 allows a step-by-step dilution in a simple and accurate manner.

The concentration of the diluted measuring sample S can be adjusted accurately by monitoring with the detection value Dt of the transmitted light Lt. It is also possible to obtain a more secure concentration by measuring the amount of the measuring sample S to be drained and the amount of the dispersion medium to be introduced.

Concentration can be determined according to Lambert-Beer's law based on a transmittance of transmitted light Lt acquired by a detector 50.

This is generally proportional to a volume concentration, wherein the volume concentration does not strictly coincide with an actual volume concentration and since relative values can be used no need arises for obtaining a strictly accurate volume concentration.

In FIG. 3, while the horizontal axis is assigned to a concentration % and the transmittance is converted to the concentration in order to obtain the value of this concentration %, it may be considered that no conversation (reduction) is applied but, in an extreme example, transmittance is directly plotted on the horizontal axis of the graph.

In the case where concentration is altered in an experiment, a sample is at first mixed into a dispersing medium while stirring it to the highest possible concentration state to obtain a suspension and it is measured to provide a concentration level therein and then, a small amount of the suspension if removed and further diluted with the dispersing medium, which is followed by repetition of the procedures of dilution to prepare a range of suspensions with different concentrations, and the concentrations are sequentially measured by irradiation.

Even by practicing a method in which a sample is added little by little to a dispersing medium, however, suspensions with different concentrations can be similarly prepared to sequentially measure the concentrations.

In addition, it is not necessarily required to alter a concentration by an increment or a decrement of 10% at a time, but a change in concentration at a time is not specifically limited as far as an approximate curve can be achieved as long as a representative range is achieved.

Sa4 is a step for determining whether the scattered light Ls can be detected or not from the diluted measuring sample S, and when it is determined that the light is within the measurable range in step Sa4, the process goes back to the step Sa1. In other words, the measuring program of the particle diameter distribution measuring device of the present embodiment increases the analysis precision by diluting the measuring sample S step by step within the range detectable by the detectors 5 and by finding the detection values of the scattered light Ls. The decisional step 4 determines if the diluted measuring sample S is over a predetermined value or alternatively if the scattering light detector output is lower than a predetermined value. This can be determined empirically by preliminary testing with reference samples of a known value. As can be determined the minimum concentration of a sample may vary depending on the type of sample. These values may be stored for reference purposes.

In the example shown in FIG. 3, the measuring sample S is measured 8 times until it is diluted to a concentration of 20%, and detection values Dx90, Dx80, Dx70, Dx60, Dx50, Dx40, Dx30, Dx20 are obtained and stored in the detection value file 15. The present embodiment takes up the example where the concentration of the measuring sample S is diluted at the rate of 10% for easier explanation; however, the present invention is not restricted to this rate and the dilution rate can be changed depending on the degree of the concentration.

It is also possible to accelerate the time required for the measurement by reducing the number of dilution steps. However, in order to calculate the approximate curve of the correction constant generation program Pb which will be described later, it is preferable to measure the sample at least 2 times (possibly 3 times or more) at different concentrations. Also, the precision of the later-described approximate curve can be further improved by diluting the concentration of the sample at more steps and increasing the number of measurements.

Figure 4:
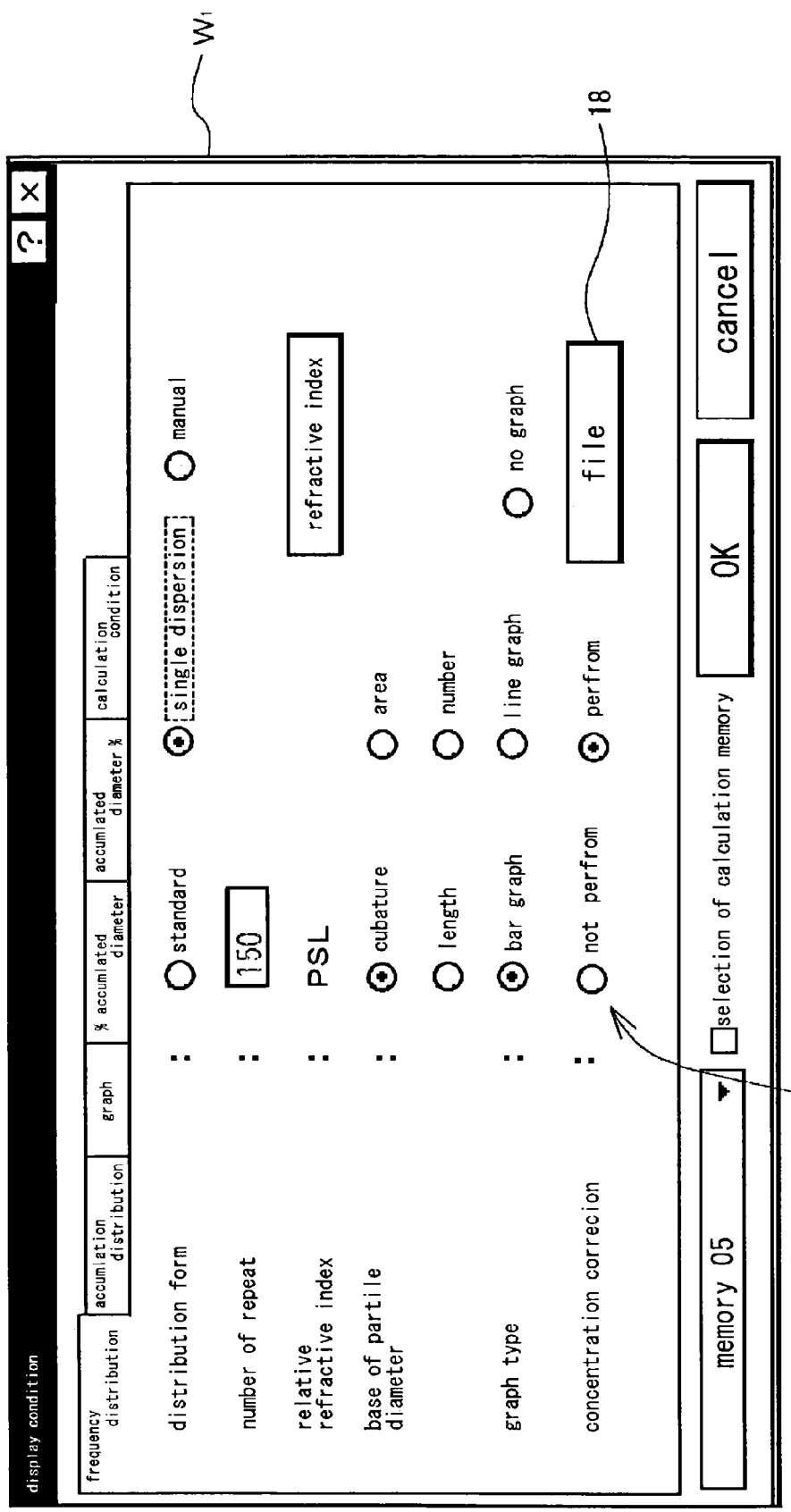
FIG. 4 shows an example of a display condition configuration screen of the particle diameter distribution measuring device.
Figure 5:
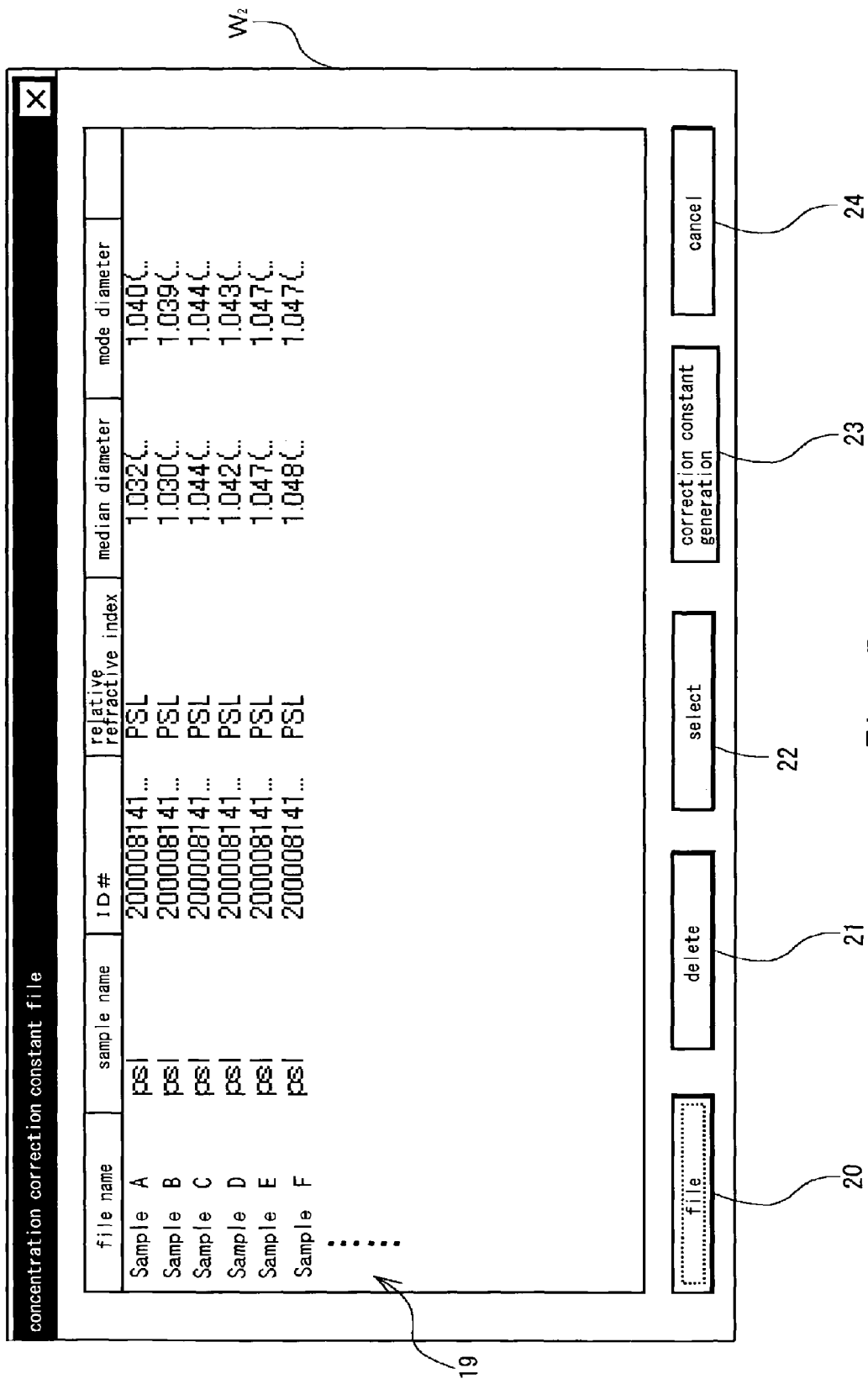
FIG. 5 shows an example of a concentration correction configuration screen of the particle diameter distribution measuring device.
Figure 6:
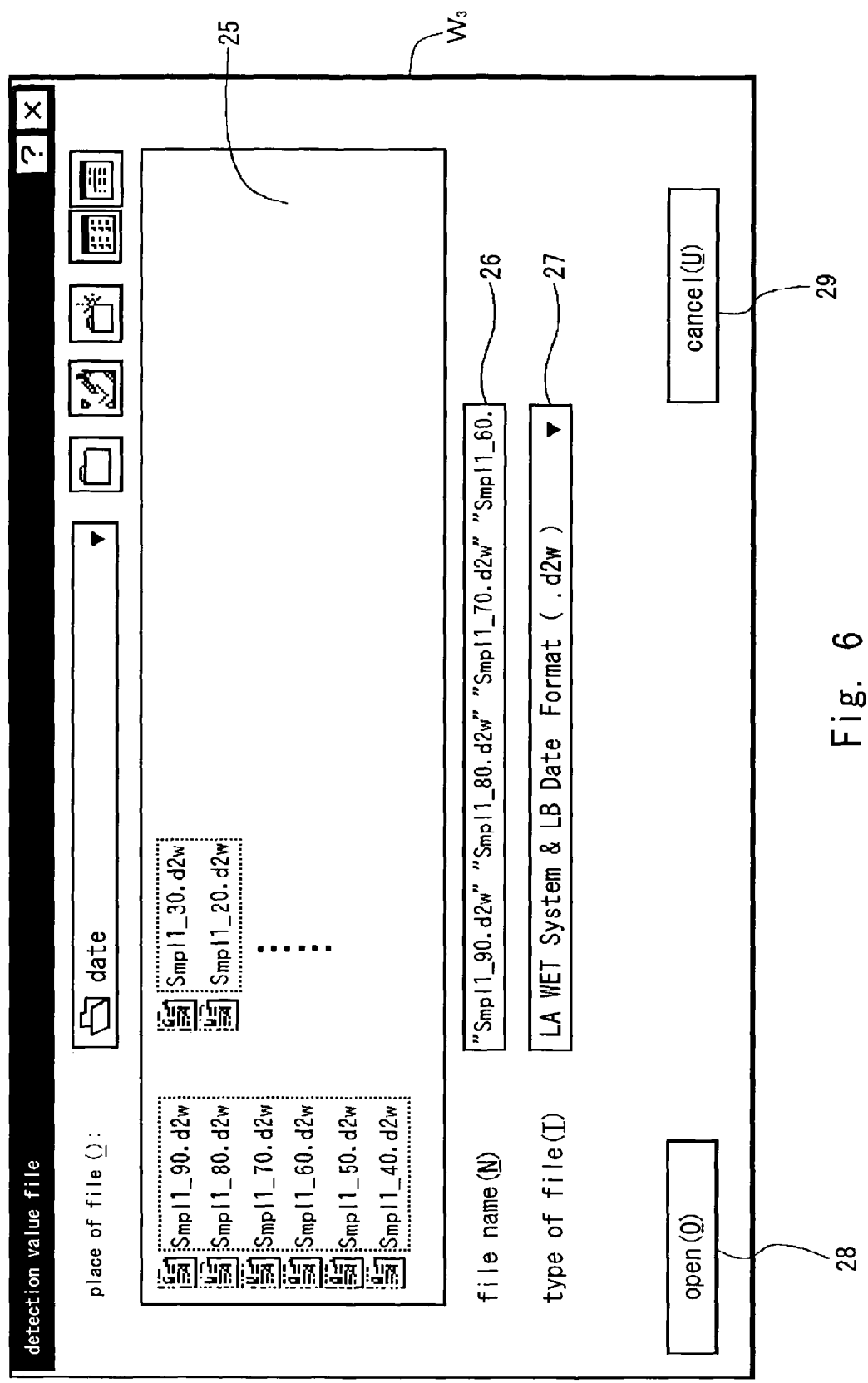
FIG. 6 shows an example of a detection value configuration screen of the particle diameter distribution measuring device.
Figure 7:
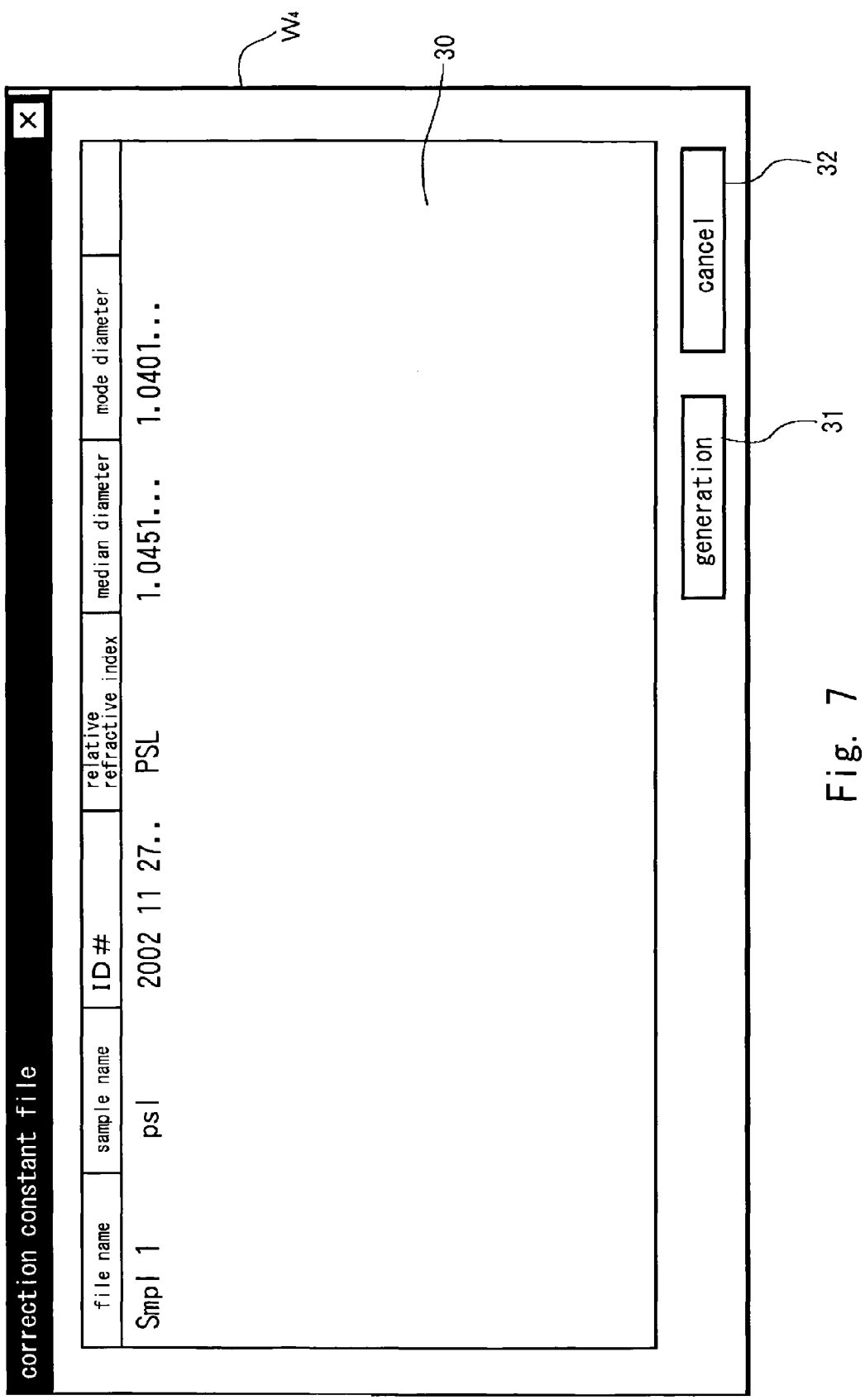
FIG. 7 shows an example of a correction constant configuration screen of the particle diameter distribution measuring device.
Figure 8:
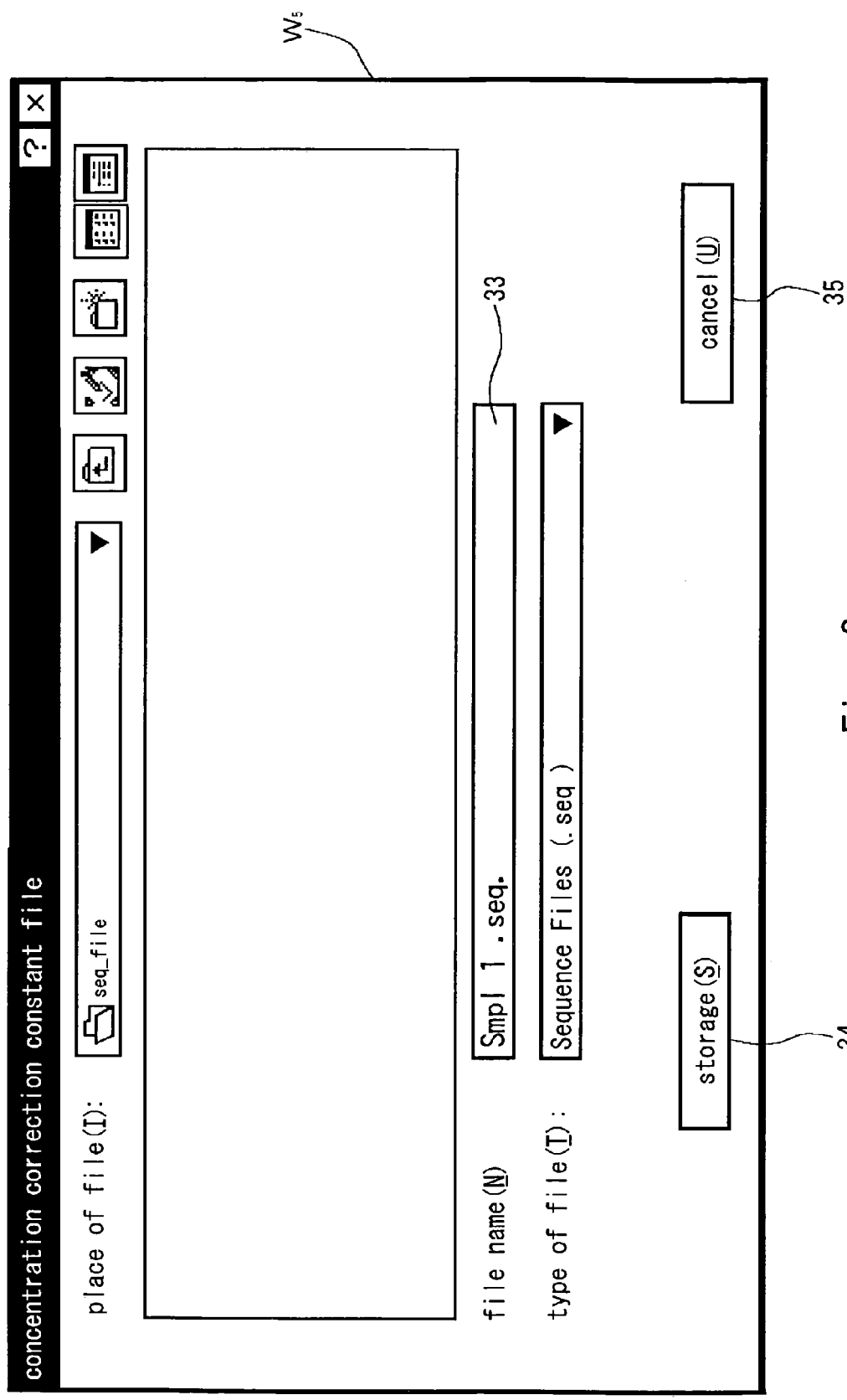
FIG. 8 shows another example of a correction constant configuration screen of the particle diameter distribution measuring device.

FIG. 4 shows a conditioning screen W1 which is displayed on the display device 7a before the execution of the correction constant generation program Pb; FIG. 5 shows a screen W2 on which the concentration correction constant file 16 is selected; FIGS. 6–8 show display screens W3–W5 which are displayed at the respective stages in the generation of the concentration correction constant.

The conditioning screen W1 shown in FIG. 4 is used to set various conditions related to the calculation of the particle diameter distribution, and is provided with a selecting part 17 which determines whether concentration correction should be performed or not; and a "file" button 18 which determines when the file is to be used for concentration correction. If the operator chooses "Yes" for concentration correction by using the selecting part 17 and clicks on the "file" button 18, then the screen W2 is displayed to show a list of the concentration correction constant files 16 shown in FIG. 5.

In FIG. 5, the reference numeral 19 represents a list display part showing a list of the concentration correction constant files 16 which can be used by the particle diameter distribution measuring device; the reference numeral 20 represents a "file" button for inputting a concentration correction constant file from outside; the reference numeral 21 represents a "delete" button for deleting the correction constant file 16 selected from the list display part 19; the reference numeral 22 represents a "select" button for selecting the correction constant file 16 selected from the list display part 19 for the calculation of a concentration correction; the reference numeral 23 represents a "correction constant generation" button for generating a new concentration correction constant file 16; and the reference numeral 24 is a "cancel" button for closing the screen $W_2$. If the operator clicks on the "correction constant generation" button 23, then the selecting screen W3 of the detection value file 15 shown in FIG. 6 is displayed on the dialog box.

In FIG. 6, the reference numeral 25 represents a list display part showing a list of the detection value files 15 accumulated so far; the reference numeral 26 represents a file name display part which displays the name of the file that the operator selects from the list display part 25; the reference numeral 27 represents a selecting part for selecting the type of the file to be displayed by the list display part 25; the reference numeral 28 represents an "open" button for opening the selected detection value file 15; and the reference numeral 29 represents a "cancel" button for suspending the generation of the concentration correction constant file. If the operator clicks on the "open" button 28 while selecting eight detection value files 15 with the file names "Smp11_20" to "Smp11_90" from the list display part 25, then the dialog box display screen W4 of the concentration correction constant file shown in FIG. 7 is displayed.

In FIG. 7, the reference numeral 30 represents a display part for displaying the file name ("Smp11" in the present embodiment) of the concentration correction constant file which is determined by the selected detection value file 15 and is newly generated; the reference numeral 31 represents a "generation" button for generating a concentration correction constant file; the reference numeral 32 represents a "cancel" button for suspending the generation of the concentration correction constant file. If the operator clicks on the "generation" button 31 at this moment, the screen W5 is displayed to register the file name of the concentration correction constant file shown in FIG. 8.

In FIG. 8, the reference numeral 33 represents an input part for inputting the file name of the concentration correction constant file which is going to be generated; the reference numeral 34 represents a "storage" button for determining the file name, executing calculation to find the concentration correction constant, and storing the calculation results; and the reference numeral 35 represents a "cancel" button for suspending the generation of a concentration correction constant file. As the file name to be inputted to the input part 33, the name common to all detection value files 15 ("Smp11" in the present embodiment) selected as default is set; however, the setting of the name can be changed variously. If the operator clicks on the "storage" button 33, then the CPU 9 executes the correction constant generation program Pb.

Figure 9:
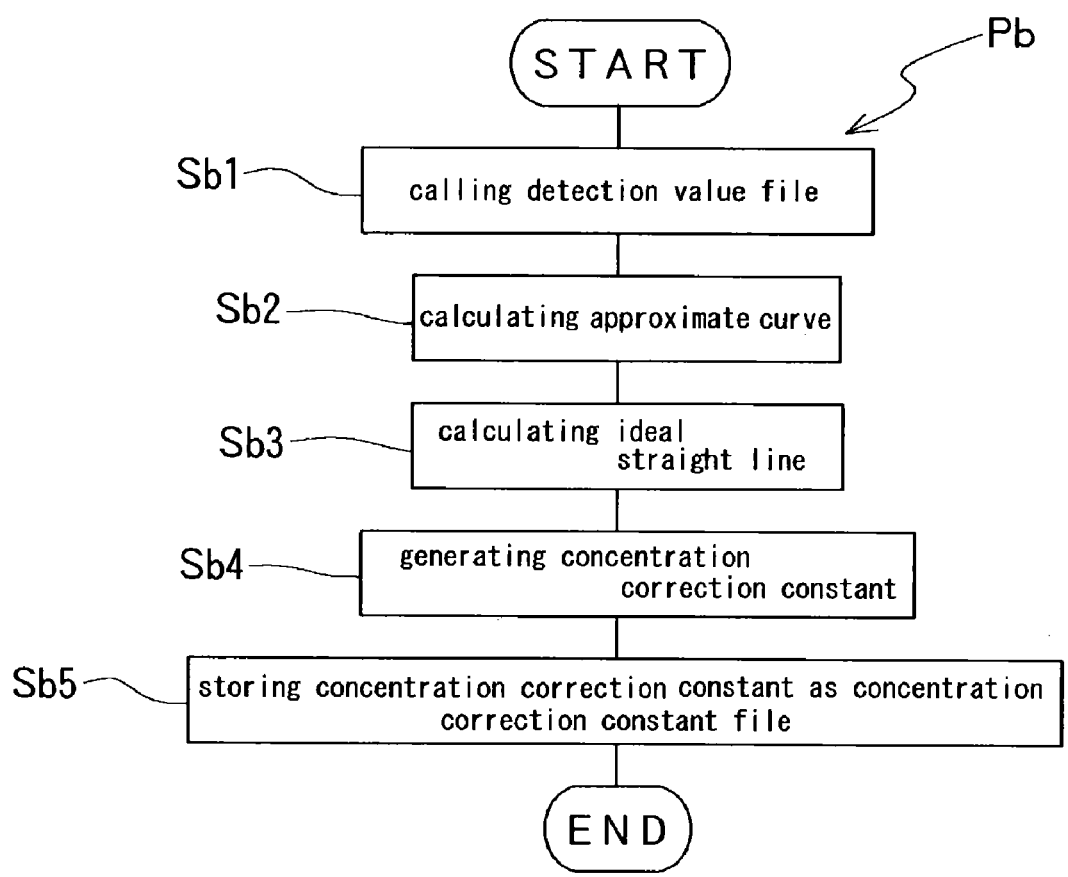
FIG. 9 shows an example of the correction constant generation program which is executed by the particle diameter distribution measuring device.

FIG. 9 shows the operation of the correction constant generation program Pb. In FIG. 9, Sb1 is a step for calling the selected detection value files 15.

Sb2 is a step for calculating the approximate curve by using each detection value Dd recorded in the selected detection value files 15. This approximate curve is generated for each detector 5, and as the approximate curve Cx in the channel X shown in FIG. 3, the detection values Dx90, Dx80 Dx70, Dx60, Dx50, Dx40, Dx30, Dx20 in the respective concentrations are approximated to a multi-dimensional function passing through the origin point by using the least-squares method or others. In the present embodiment, for easier explanation, the detection values from the detectors 5 are completely corrected to the zero position.

The calculation in the step Sb2 is executed the same number of times as the number of channels in the detector 5, and is stored as the constants to draw the respective approximate curves. The present invention does not restrict the approximate curve to a multiple function, and it can be approximated by logarithm or various functions such as trigonometric function. In addition, the calculation to find the approximate curve is not restricted to the least-squares method.

Sb3 is a step for calculating and finding the ideal proportionality between the concentration and the detection value by using the approximate curve. For example, from the inclination of the approximate curve when the concentration is zero, the ideal proportionality indicative of the relation between the detection value and the concentration of the measuring sample S is found.

To be more specific, as apparent from the approximate curve Cx shown in FIG. 3, the detection value Dx20 obtained when the measuring sample S has a low concentration has little deviation from an ideal value. This indicates that the inclination of the approximate curve Cx when the concentration is zero is not affected by multiple scattering or absorption. Since the concentration and the detection value Dx ideally have proportionality (direct proportionality when the offset is completely corrected), the straight line Lx indicative of the proportionality of the same inclination as the inclination of the approximate curve Cx when the concentration is zero has the ideal proportionality.

Thus the slope of the ideal straight line or proportionality can be derived from a detection value Dx20 that is substantially free of any concentration errors and extended to a zero value. This proportionality can be further extended through the range of concentration of particles that have an effect on the detector measurements.

Sb4 is a step for generating a concentration correction constant by using the ideal proportionality with the approximate curve. According to a specific example using FIG. 3, the result of the subtraction of the relational expression indicative of the ideal straight line Lx from the relational expression indicative of the approximate curve Cx becomes the concentration correction constant, and as shown in the shaded area E, the concentration correction constant can find the size of the influence of the distortion that should be subtracted from the actual measurement value Dx. A concentration correction constant is found for each channel in the detectors 5.

Sb5 is a step for storing the obtained concentration correction constant as a concentration correction constant file 16. In the present embodiment, the concentration correction constant file 16 is stored with the file name "Smp11" determined in the screen W5 shown in FIG. 8. As a result, the concentration correction constant file 16 is used to measure the particle diameter distribution of a measuring sample S of the same kind.

As can be appreciated, a known set of correction constants derived from a calibration sample of a specific sample can than be stored and used to determine the particle diameter distribution of an unknown sample of the same kind of particles.

Figure 10:
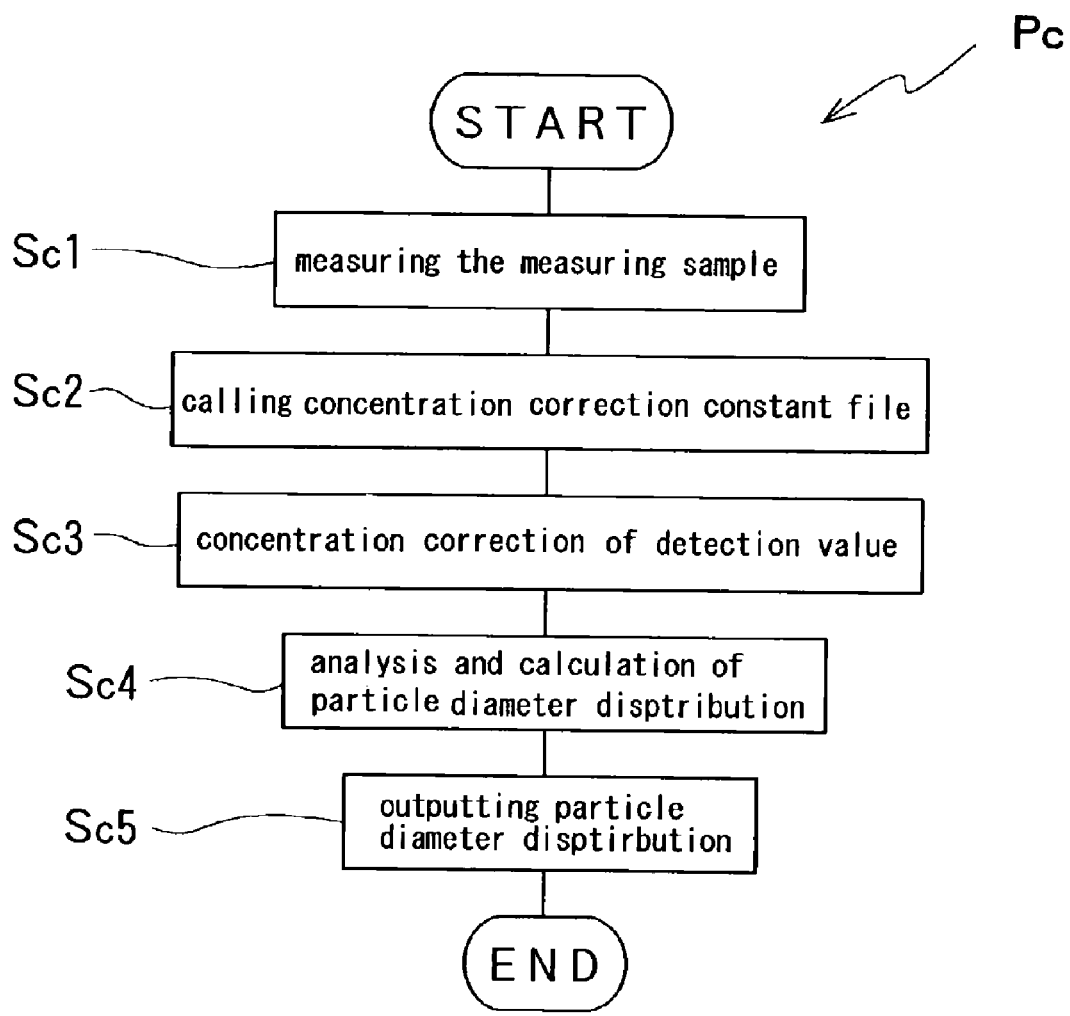
FIG. 10 shows an example of the particle diameter distribution analyzing program which is executed by the particle diameter distribution measuring device.

FIG. 10 shows the operation of the particle diameter distribution analyzing program Pc. In FIG. 10, Sc1 is a step for measuring the measuring sample S, and to be more specific, the intensity of the scattered light Ls obtained by radiating the measuring sample S with the light L is found from the detection value Dd for each detector 5.

Sc2 is a step for selecting and calling the concentration correction constant file 16 generated by using the same (kind of) sample as the measuring sample S used this time. To be more specific, the concentration correction constant file 16 with the file name (e.g. "Smp11") selected in accordance with the setting of the file used for concentration correction already described by referring to FIGS. 4 and 5 is read from the supplementary storage device 8b.

Sc3 is a step for performing the concentration correction of the detection value Dd by using the concentration correction constant file 16. The processing of the step Sc3 to correct the detection value Dx in the channel X will be shown specifically by using FIG. 3. Assume that the concentration of the measuring sample S is measured by using the detection value Dt of the transmitted light Lt which has transmitted through the measuring sample S, and that the concentration is 77%. Then, assume that the detection value Dx in the channel X from the detector 5 has the size of Dx77.

Through the processing of the step Sc3, the detection value Dx77 is found to contain error Ex77, which is then subtracted. In other words, even if the detection value Dx77 indicated by the symbol ○ in FIG. 3 is inputted, this is corrected to the ideal value Dx77t indicated by the symbol ◇. The correction of the detection value Dd is performed in every channel.

The concentration of the detection value Dd does not necessarily have to be found from the detection value Dt of the transmitted light Lt. With reference to FIG. 3, it is possible to find the ideal value Dx77t by finding the concentration with the use of the approximate curve Cx from the detection value Dx77 obtained when the measuring sample S whose concentration is unknown is measured.

In order to make the explanation easy to understand, the above description shows in FIG. 3 the relation between the detection values Dx20–Dx90 and the concentration of the measuring sample S; however, the concentration of the measuring sample S (diluting rate) is generally determined by the detection value Dt of the transmitted light Lt. To be more specific, the relation between the detection value Dx of each detector 5 and the concentration of the measuring sample S in the present specification includes the relation between the detection value Dx of each of the detectors 5a, 5b and the detection value Dt of the transmitted light measured by the detector 5o. The analysis and calculation of the particle diameter distribution could be found by correcting the detection value Dx of each of the detectors 5a, 5b not in the relation with the concentration but in the relation with the detection value Dt of the transmitted light.

Sc4 is a step for performing the analysis and calculation of the particle diameter distribution by using the detection value Dx77t which has been corrected to an ideal value. The analysis and calculation of the particle diameter distribution is performed after removing error resulting from the influence of multiple scattering or absorption from the detection value Dd. Therefore, the analysis and calculation of the particle diameter distribution can be performed at an extremely high precision, without being influenced by the concentration of the measuring sample S.

Sc5 is a step for outputting the particle diameter distribution obtained in the processing of the step Sc4. This output can be done by displaying the analysis results of the particle diameter distribution on the display device 7a and/or by storing the analysis results in a file.

In the case where the properties of the measuring sample S are clearly known, the above-described series of calculations can be performed to reduce the concentration dependence and to increase the analysis precision as much as possible. This is extremely useful, for example, when the particle diameter distribution is controlled in the process of fabrication of a medicine or when the particle diameter distribution of ink for an ink jet printer is controlled. However, the particle diameter distribution measuring device of the present invention is useful in measuring the particle diameter distribution of other types of measuring samples.

In each example mentioned above, each of the programs Pa, Pb, and Pc generates or uses the detection value files 15 and the concentration correction constant files 16, making it possible to temporally separate the execution of each of the programs Pa, Pb, and Pc. Therefore, it is possible to find in advance several detection value files 15 and concentration correction constant files 16 of plural samples which can be the measuring sample S, later to select the concentration correction constant file 16 of the sample corresponding to the measuring sample S, and to measure its particle diameter distribution. For example in diluting a sample of a high concentration detection values can be stored and after a sufficient dilution the necessary ideal proportionately can be determined to enable the subsequent concentration constants to be derived from the stored detection values. It is also possible to find the programs Pa and Pb by a particle diameter distribution measuring device and to use the detection value files 15 and/or the concentration correction constant files 16 in another particle diameter distribution measuring device.

Figure 11:
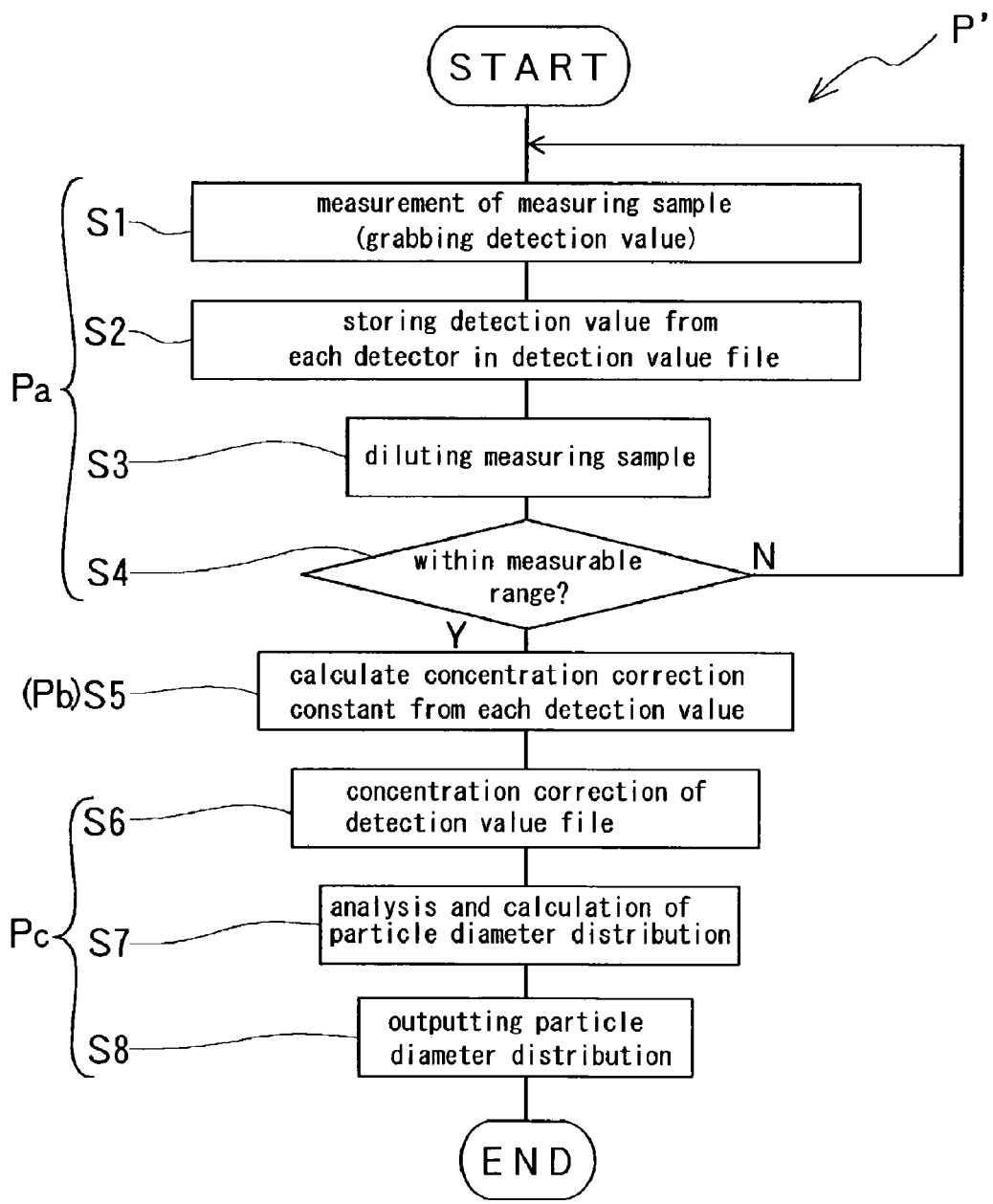
FIG. 11 shows an example of a series of measuring program steps which are executed by the particle diameter distribution measuring device.

However, the present invention is not restricted to separating the programs Pa–Pc. FIG. 11 shows an example of the measuring program P' executing a series of operations in which the analysis and calculation of the particle diameter distribution is performed after the concentration correction constant is obtained, with regard to a measuring sample whose concentration correction constant file has not been generated yet.

In FIG. 11, S1–S4 are steps for executing the processings corresponding to the steps Sa1–Sa4 of the detection value grabbing program Pa, and S5 is a step for executing the processings corresponding to the steps Sb2–Sb4 of the correction constant generation program Pb (the detailed procedure of generating the correction constant will be omitted). In the present embodiment, the series of operations for the analysis and calculation of the particle diameter distribution are performed by the single measuring program P', so that the concentration correction constant can be found by using the detection value of the measuring sample grabbed in step S1. In this case, it is not always necessary to store the obtained concentration correction constant as a file.

S6–S8 are steps corresponding to the steps Sc3–Sc5 of the particle diameter analysis program Pc, in which the concentration of the detection value of the measuring sample grabbed in the step S1 is corrected and then the corrected value is used for the analysis and calculation of the particle diameter distribution. Therefore, in the measuring program P' for the particle diameter distribution measuring device of the present embodiment, a particle diameter distribution of the measuring sample S which is totally unknown can be measured at high precision. With regard to a sample whose correction constant file has been already prepared, this series of operations can be performed with the advantage of eliminating the need for the selecting operation of the concentration correction constant file 16 as shown in FIGS. 5 to 8.

In the present embodiment, at the point when the inclination of the ideal straight line Lx shown in FIG. 3 is found, this inclination can be used as the detection value for the analysis and calculation of the particle diameter distribution. To be more specific, the particle diameter distribution measuring device 1 of the present invention, which executes the measuring program P', can have further improved measuring precision because the concentration of the measuring sample S is diluted step by step by the automatic dilution unit 11; the detection values of the detectors 5 are stored separately for each concentration; and the particle diameter distribution is analyzed by using all the detection values Dd stored. In addition, the particle diameter distribution can be found with high precision which is not influenced by error resulting from the concentration of the measuring sample.

As described hereinbefore, according to the present invention, particle diameter distribution can be measured more precisely by setting the concentration correction constant unique to the measuring sample in order to reduce the concentration dependence, without diluting the concentration of the measuring sample to the proper range for particle diameter distribution.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A particle size distribution device for measuring the size of particles by irradiating the particles in a carrier medium with radiation that can be diffracted and/or scattered by the particles and detected by a plurality of detectors, comprising:
    a radiation unit for applying radiation to a measurement cell;
    a concentration level adjusting unit for changing a relative amount of particles to an amount of carrier medium to be applied to the measurement cell;
    a storage device for storing the outputs of the detectors for each concentration level irradiated;
    a correction unit for providing a concentration correction constant; and
    a calculating unit for providing particle size distribution outputs from the outputs of the detectors as adjusted by the concentration correction constant.

2. The particle size distribution device of claim 1 wherein the correction unit generates a proportional relationship between concentration levels and corresponding detector outputs and adjusts the measured detector outputs relative to the proportional relationship to provide a concentration correction constant.

3. The particle size distribution device of claim 2 wherein the concentration level adjusting unit provides a concentration level that is substantially free of concentration errors in the detectors to enable a determination of the proportional relationship.

4. The particle size distribution device of claim 2 wherein the calculating unit subtracts a concentration correction constant from each of the detectors outputs to enable a determination of the particle size distribution.

5. In a particle size distribution device for measuring the size of particles by irradiating the particles in a carrier medium with radiation and detecting the influence of the particles on the radiation, the improvement of enabling a compensation for the amount of particles in the medium, comprising:
    a concentration level adjusting unit for changing a relative amount of particles to an amount of carrier medium to enable measurements of an influence of particles on the radiation that are substantially free from an effect relating to a level of concentration of particles to the carrier medium; and
    a correction unit for generating a proportional relationship between the amount of particles in the carrier medium and the output of the detectors, substantially free from an effect relating to the level of concentration of particles to the carrier medium, based on measurements form the concentration level adjustment unit to enable a calculation of concentration correction constants.

6. A method of correcting for concentration errors generated by particles in a carrier medium that are irradiated and measurements are taken by detectors, comprising the steps of:

deriving a proportional relationship between the amount of particles in the carrier medium and an output of detectors in a concentration range substantially free from an effect relating to the level of concentration of particles to the carrier medium;

extending the proportional relationship through concentration ranges that have an effect relating to the level of concentration of particles to the carrier medium; and determining concentration correction constants from a difference between the proportional relationship and detector outputs in the concentration ranges that have an effect relating to the level of concentration of particles to the carrier medium.

7. A particle diameter distribution measuring method for measuring the particle diameter distribution of a measuring sample, based on the detection values of plural detectors provided for detecting at predetermined angles diffracted light and/or scattered light generated when light is applied to the measuring sample comprising the steps of:

storing the output of the respective detectors at different concentrations of the measuring sample;

determining concentration correction constants for correcting the detection values of the respective detectors at different concentrations of the sample;

correcting detection values of the respective detectors by using the concentration correction constants, and determining the particle diameter distribution by using the corrected detection values of the respective detectors.

8. A particle diameter distribution measuring device for measuring particle diameter distribution of a measuring sample, based on the detection values of plural detectors provided for detecting at predetermined angles diffraction light and/or scattered light generated when light is applied to the measuring sample, comprising:

a storage part which stores the detection values of the detectors separately for each concentration of measuring sample and carrier fluid when the measuring sample is diluted to different concentrations; and an arithmetic processing part for generating concentration correction constants to remove an influence of error resulting from the concentration of the measuring sample separately for each detector by analyzing the detection values of the detectors stored in the storage part in association with the concentrations of the measuring sample.

9. A particle diameter distribution measuring device for measuring the particle diameter distribution of a measuring sample, based on the detection values of plural detectors provided for detecting at predetermined angles diffraction light and/or scattered light generated when light is applied to the measuring sample, comprising:

a storage part which stores concentration correction constants obtained by finding the amount of correction in the detection values of the detectors in accordance with different concentrations of the measuring sample, based on the detection values of the detectors measured a plural number of times by changing the concentration of the measuring sample in a carrier fluid; and an arithmetic processing part which corrects the detection values of the detectors in accordance with the concentrations of the measuring sample by using the concentration correction constants, and then calculates the particle diameter distribution by using the corrected detection values.

10. A measuring program executed by a particle diameter distribution measuring device for measuring the particle diameter distribution of a measuring sample, based on the detection values of plural detectors provided for detecting at predetermined angles diffraction light and/or scattered light generated when light is applied to the measuring sample, comprising measuring a measuring sample diluted to different concentrations and storing the detection values of the detectors separately for each concentration with a detection value grabbing program module; and analyzing the detection values of the detectors in association with the concentrations of the measuring samples and finding the concentration correction constants for each detector which removes the influence of error resulting from concentration with a correction constant generation program module.

11. The measuring program of claim 10 wherein the correction constant generation program module comprises: an approximate curve calculation step for finding an approximate curve indicative of a relation between the detection values and the concentration of a measuring sample; an ideal value calculation step for finding the ideal proportionality indicative of the relation between the detection values and the concentration of the measuring sample from the inclination of the approximate curve at the time when the concentration is zero; and a correction constant generation step for finding the concentration correction constant to remove an influence of error resulting from the concentration based on the difference of the detection values with respect to the ideal proportionality.

12. A measuring program executed by a particle diameter distribution measuring device for measuring the particle diameter distribution of a measuring sample, based on the detection values of plural detectors provided for detecting at predetermined angles diffraction light and/or scattered light generated when light is applied to the measuring sample, comprising:

determining detection values of the respective detectors for different concentrations of the measuring sample to the carrier medium;

determining concentration correction constants from the detection values;

correcting the detection values with the concentration correction constants; and determining the particle diameter distribution from the correction detection values.

* * * * *